United States Patent
Schmidt et al.

(10) Patent No.: US 6,632,835 B2
(45) Date of Patent: Oct. 14, 2003

(54) DIBENZO[C]CHROMEN-6-ONE DERIVATIVES AS ANTI-CANCER AGENTS

(75) Inventors: Jonathan Martin Schmidt, Elora (CA); Peter Redden, Oakville (CA); Julie Mercure, Guelph (CA); Shuguang Zhu, Seattle, WA (US); John Whelan, Toronto (CA); Natalie Lazarowych, Richmond Hill (CA)

(73) Assignee: Nanodesign Inc., Montreal (CA)

(*) Notice: Subject to any disclaimer, the term of this patent is extended or adjusted under 35 U.S.C. 154(b) by 0 days.

(21) Appl. No.: 09/934,086

(22) Filed: Aug. 21, 2001

(65) Prior Publication Data

US 2002/0115711 A1 Aug. 22, 2002

Related U.S. Application Data

(60) Provisional application No. 60/270,198, filed on Feb. 22, 2001.

(51) Int. Cl.$^7$ .............................................. A61K 31/35
(52) U.S. Cl. ...................... 514/455; 514/452; 549/280
(58) Field of Search .................... 549/280; 514/452, 514/455

(56) References Cited

U.S. PATENT DOCUMENTS

| | | | |
|---|---|---|---|
| 5,504,074 A | 4/1996 | D'Amato et al. | 514/182 |
| 5,593,990 A | 1/1997 | D'Amato | 514/235.2 |
| 5,610,166 A | 3/1997 | Singh | 514/324 |
| 5,629,327 A | 5/1997 | D'Amato | 514/323 |
| 5,643,900 A | 7/1997 | Fotsis et al. | 514/182 |
| 5,646,136 A | 7/1997 | Petrow et al. | 514/167 |
| 5,696,147 A | 12/1997 | Galardy | 514/419 |
| 5,712,291 A | 1/1998 | D'Amato | 514/323 |
| 5,733,876 A | 3/1998 | O'Reilly et al. | 514/12 |
| 5,753,230 A | 5/1998 | Brooks et al. | 424/158.1 |
| 5,763,441 A | 6/1998 | App et al. | 514/249 |
| 5,843,925 A | 12/1998 | Backer et al. | 514/152 |

OTHER PUBLICATIONS

Perry JD et al 'idenification of salmonella' CA 130:49520 (1998).*
Auerbach and Auerbach, "Angiogenesis inhibition: a review," *Pharmacol Ther.*, 63(3):265–311, 1994.
Beck and D'Amore, "Vascular development: cellular and molecular regulation," *FASEB J.*, 11:365–373, 1997.
Blagosklonny et al., "Taxol–induced apoptosis and phosphorylation of Bcl–2 protein involves c–Raf–1 and represents a novel c–Raf–1 signal transduction pathway," *Cancer Res.*, 56:1851–1854, 1996.
Colville–Nash and Willoughby, "Growth factors in agiogenesis: current interest and therapeutic potential," *Molecular Medicine Today*, 14–23, 1997.
Coomber and Gotlieb, "In vitro endothelial wound repair," *Arteriosclerosis*, 10(2):215–222, 1990.

Eckhardt and Pluda, "Development of angiogenesis inhibitors for cancer therapy," *Investigational New Drugs*, 15:1–3, 1997.
Fan et al., "Controlling the vasculature: angiogenesis, anti–angiogenesis and vascular targeting of gene therapy," *TiPs*, 16:57–66, 1995.
Gagliardi and Collins, "Inhibition of angio genesis by anti–estrogens," *Cancer Res.*, 53: 533–535, 1993.
Gastl et al., "Angiogenesis as a target for tumor treatment," *Oncology*, 54:177–184, 1997.
Harris et al., "Breast cancer angiogenesis—new approaches to therapy via antiangiogenesis, hypoxic activated drugs, and vascular targeting," *Breast Cancer Res. And Treatment*, 38:97–108, 1996.
Jain et al., "Quantitative angiogenesis assays: progress and problems," *Nature Medicine*, 3(11):1203–1208, 1997.
Kumar et al., "Regulation of distinct steps of angiogenesis by different angiogenic molecules," *Int. J. of Oncology*, 12:749–757, 1998.
LaBudde and Heidelberger, "The synthesis of the Mono– and dihydroxy derivatives of 1,2,5,6–Dibenzanthracene excreted by the rabbit and of other hydroxylated dibenzanthracene derivatives," *Synthesis of Hydroxylated Dibenzanthracenes*, 80:1225–1236, 1958.
Maier et al., "In vitro inhibition of endothelial cell growth by the antiangiogenic drug AGM–1470 (TNP–470) and the anti–endoglin antibody TEC–11," *Anti–Cancer Drugs*, 8:238–244, 1997.
Matsubara et al., "Inhibition of human endothelial cell proliferation in vitro and neovascularization in vivo by D–Penicillamine," *J. Clin. Invest.*, 83:158–167, 1989.
Mousa, "Mechanisms of angiogenesis in vascular disorders: potential therapeutic targets," *Drugs of the Future*, 23(1):51–60, 1998.
Nelson, "Inhibitors of angiogenesis enter phase III testing," *J. of the Nat'l Cancer Institute*, 90(13):960–963, 1998. Article found at the Journal of the National Cancer Institutes Website: http//jnci.oupjournals.org/cgi/content/...volume= 960 90&firstpage=&journalcode=jnci, Oct. 12, 2001.
O'Reilly, "The preclinical evaluation of angiogenesis inhibitors,"*Investigational New Drugs*, 15:5–13, 1997.
Pluda, "Tumor–associated angiogenesis: mechanisms, clinical implications, and therapeutic strategies, " *Seminars in Oncology*, 24(2):203–218, 1997.
Risau, "Mechanisms of angiogenesis," *Nature*, 386:671–674, 1997.

(List continued on next page.)

Primary Examiner—Amelia A. Owens
(74) Attorney, Agent, or Firm—Fulbright & Jaworski L.L.P.

(57) ABSTRACT

Molecules demonstrating anti-proliferative effects against epithelial cancer cell lines and endothelial cells and methods of synthesis are disclosed. The molecules are intended for use in therapeutic preparations for the treatment of cancer through either anti-angiogenesis or other anti-cancer mechanisms. The compounds specified are 6H-dibenzo[b,d]pyran-6-one derivatives and have been shown to be antiproliferative against human endothelial cells.

14 Claims, 4 Drawing Sheets

OTHER PUBLICATIONS

Szekanexz et al., "Angiogenesis in rheumatoid arthritis: pathogenic and clinical significance," *J. of Invest. Medicine*, 46(2):27–41, 1998.

Twardowski et al., "Clinical trials of antiangiogenic agents," *Current Opinion in Oncology*, 9:584–589, 1997.

Yamamoto et al., "Significant inhibition of endothelial cell growth in tumor vasculature by an angiogenesis inhibitor, TNP–470 (AGM–1470)," *Anticancer Res.*, 14:1–4, 1994.

Zetter, "Angiogenesis and tumor metastasis," *Annu. Rev. Med.*, 49:407–423, 1998.

* cited by examiner

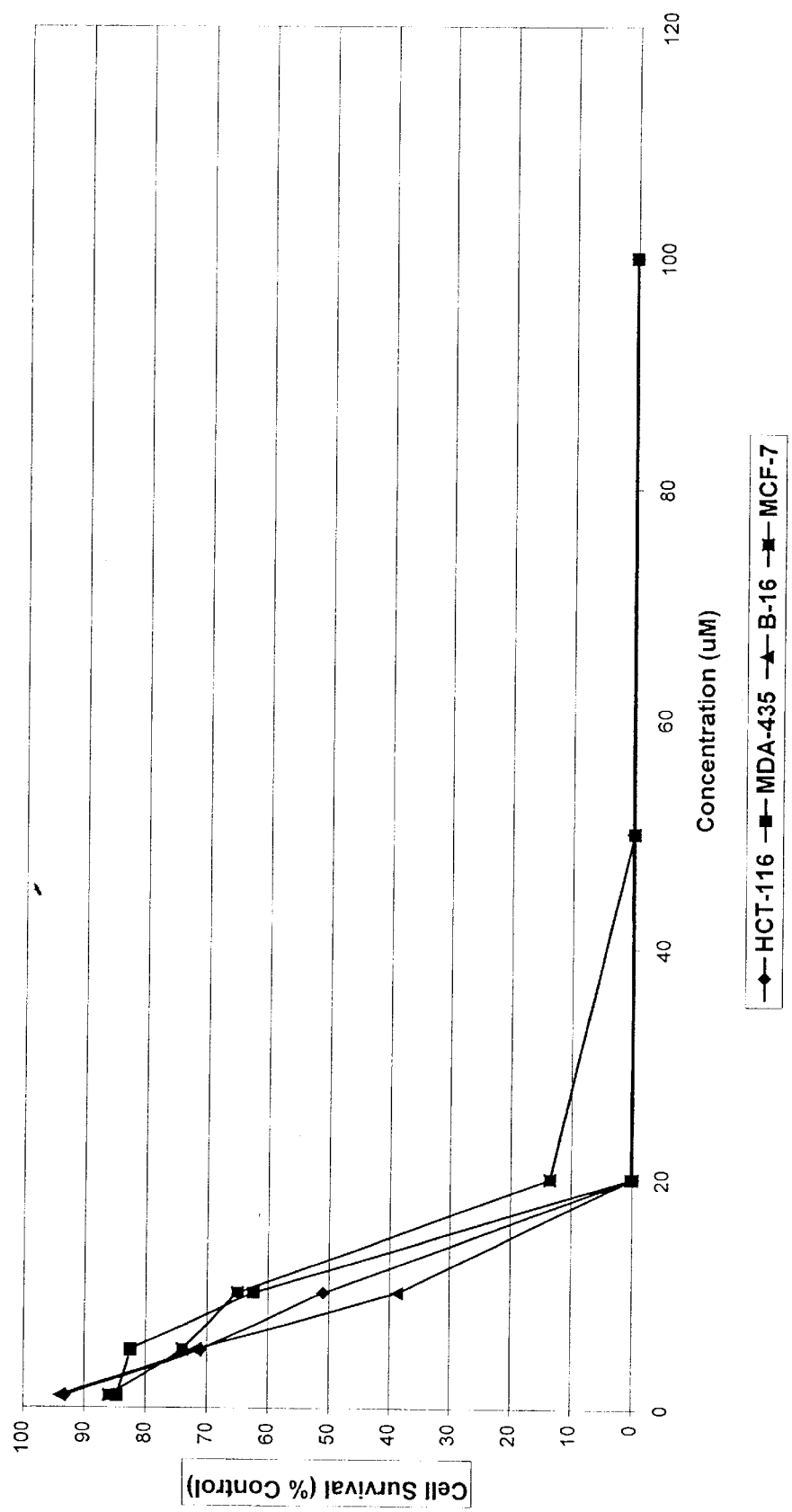

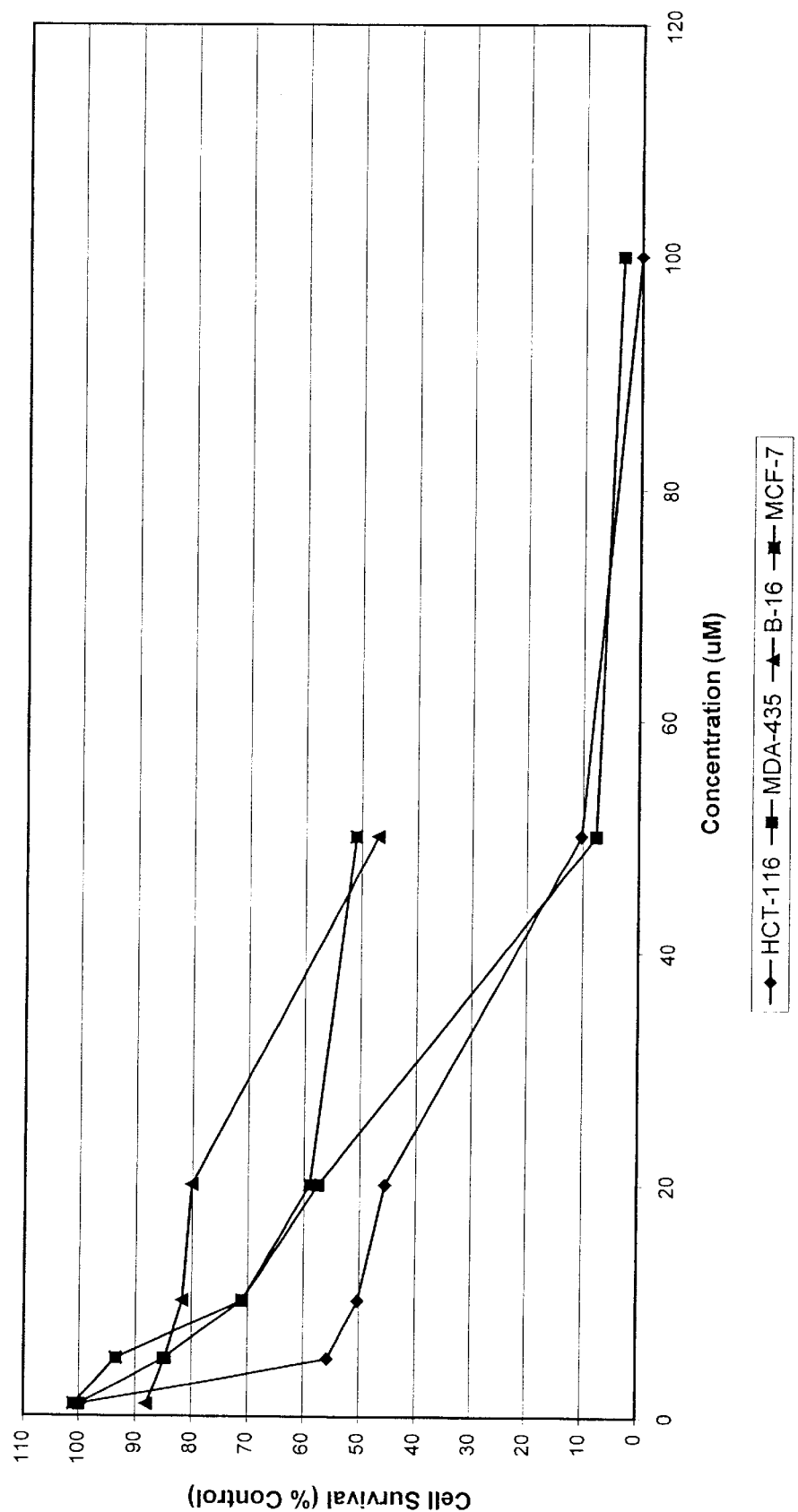

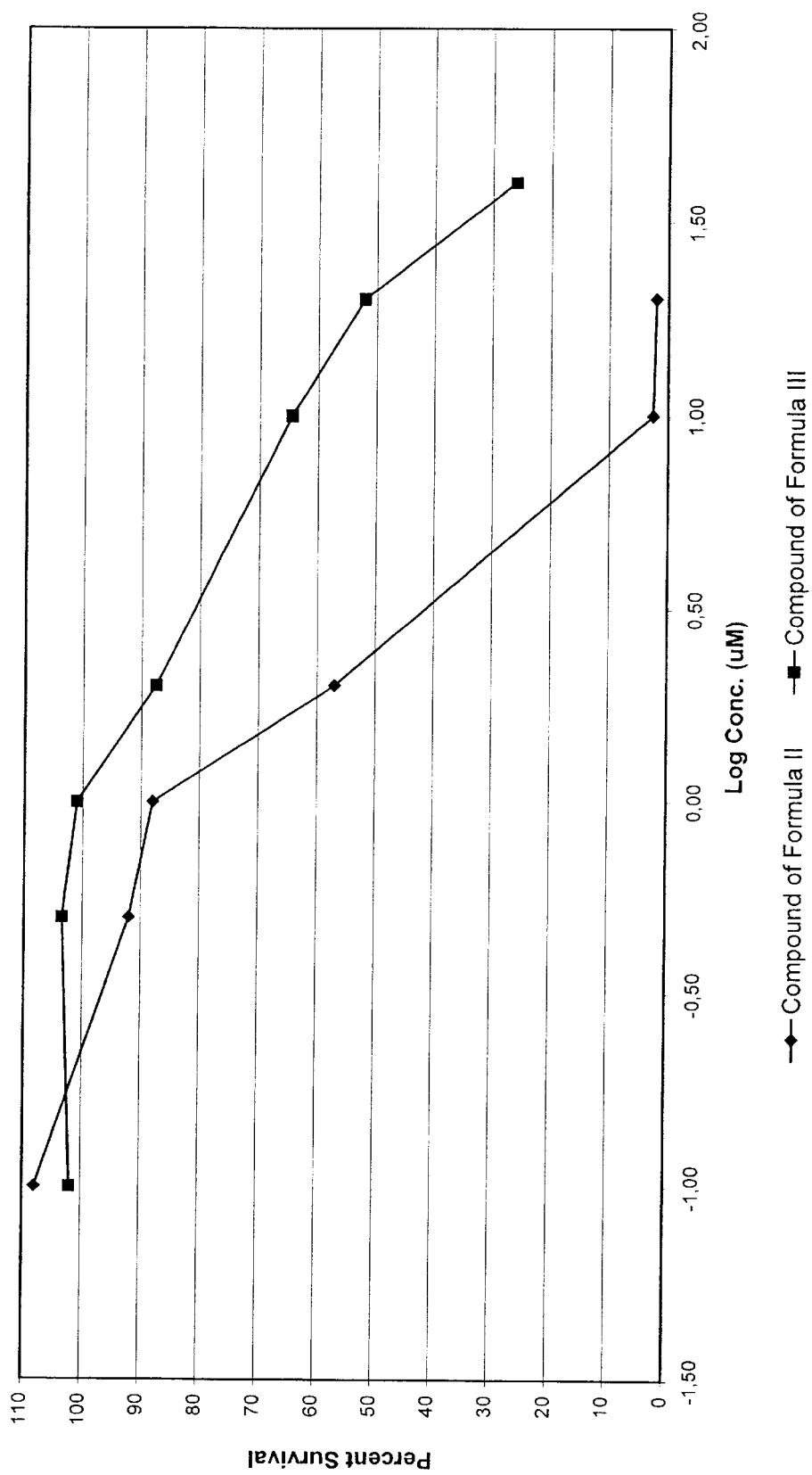

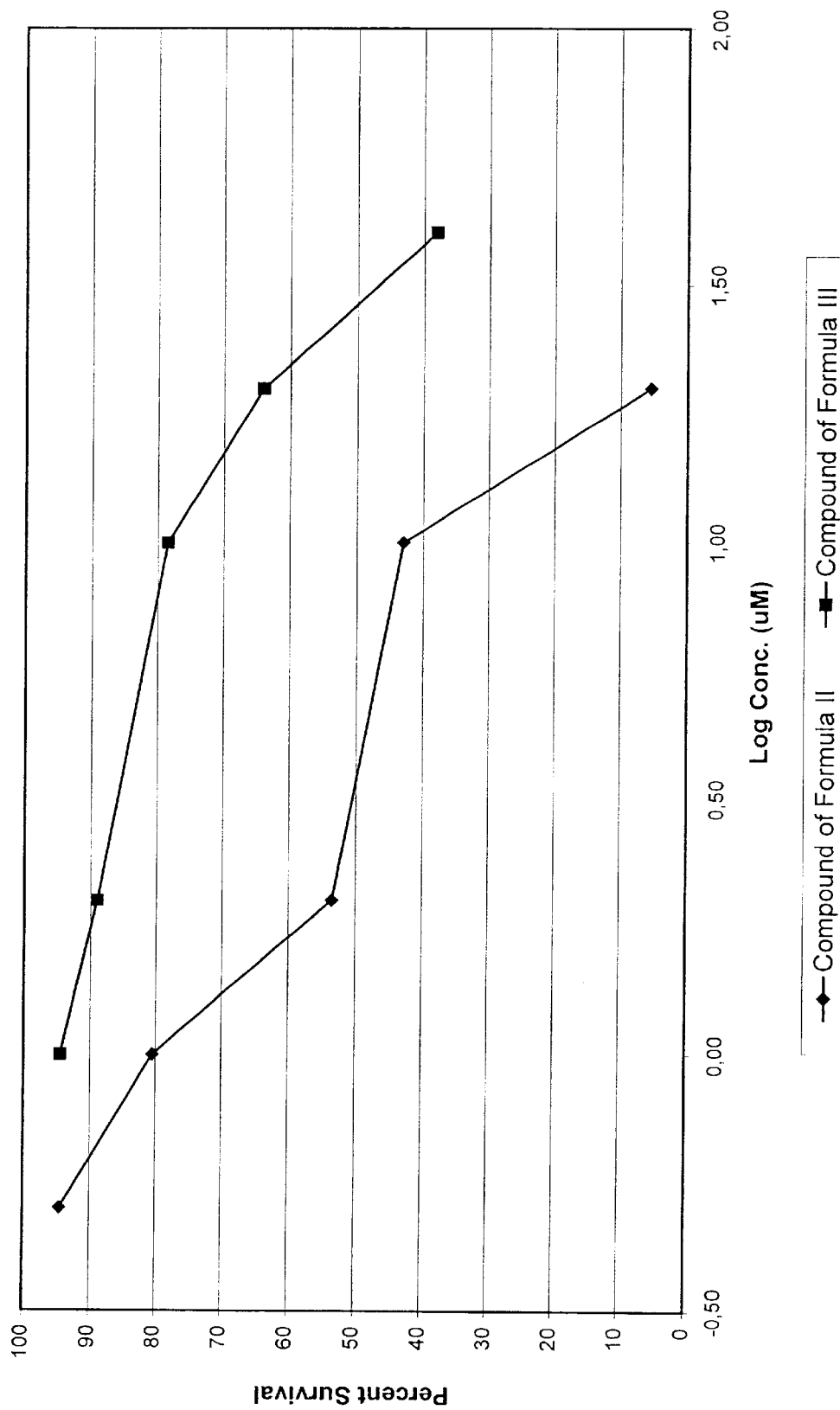

DIBENZO[C]CHROMEN-6-ONE DERIVATIVES AS ANTI-CANCER AGENTS

This application claims priority to pending provisional patent application Ser. No. 60/270,198, filed Feb. 22, 2001.

FIELD OF THE INVENTION

The present invention relates to a series of new chemical agents that demonstrate anti-proliferative effects against human endothelial cells for the treatment of a variety of diseases including cancer, in addition to an inhibitory effect directly on cancer cells for the treatment of solid tumors. More particularly, the present invention relates to molecules that demonstrate anti-proliferative capabilities against human endothelial cells and several epithelial cancer cells and their applications in treating a variety of disease states.

BACKGROUND OF THE INVENTION

Cancer is a disease state characterized by the uncontrolled proliferation of genetically altered tissue cells. There have been several chemotherapeutic approaches targeted against such proliferation including alkylating agents, antimitotics, antimetabolites, and antibiotics. These act preferentially on rapidly proliferating cells including cancer cells. Hormonal therapy with anti-estrogens or anti-androgens is another approach to attacking cancer cells that work by inhibiting the proliferative action of the required hormone. Although anti-cancer agents fall into specific classifications, it is not uncommon for agents to act by multiple modes of action. For example, the anti-estrogen tamoxifen has been shown to have anti-proliferative activity on cancer cells and endothelial cells by an estrogen independent mechanism. Taxol, an antimitotic agent acting on microtubules has also demonstrated antiangiogenic properties, possibly by inducing apoptosis through Bcl-2 phosphorylation.

Angiogenesis, the formation of new blood vessels, is a fundamental biological process involved in wound healing, tissue regeneration, embryogenesis and the female reproductive cycle. Blood vessel walls are formed by endothelial cells that have the ability to divide and migrate under specific stimuli, such as growth factors. The creation of new blood vessels follows a specific set of tightly regulated steps. Briefly, endothelial cells are stimulated by factors secreted by surrounding cells and secrete enzymes such as matrix metalloproteinases that break down the extra-cellular matrix and basement membrane, thus creating a space for the cells to migrate into and establish themselves. The endothelial cells then organize into hollow tubes that eventually form a new vascular network of blood vessels providing surrounding cells with nutrients and oxygen and the ability to eliminate toxic metabolic waste products. Under normal physiological conditions endothelial cells are dormant unless triggered to proliferate in localized parts of tissues. Many diseases are associated with the inappropriate proliferation of endothelial cells including arthritis, psoriasis, arteriosclerosis, diabetic retinopathy, and cancer.

In order for a tumor to grow beyond a few million cells, typically more than 1 or 2 $mm^3$ in volume, an increase in vascularization is required. Cells that are too distant from blood vessels cannot survive because of poor nutrient and oxygen supply. Clinically, tumors that are highly vascularized are the most metastatic and difficult to treat. It is also known that tumor cells produce and secrete the factors necessary for angiogenesis. It is widely held that agents inhibiting angiogenesis through direct competition with angiogenic factors, or by some other mechanism, would have a major clinical benefit in the treatment of many types of cancer and other diseases associated with inappropriate angiogenesis.

Many therapeutic agents are being targeted for development based on a variety of targeting strategies. One strategy is the use of natural inhibitors of angiogenesis such as angiostatin and endostatin. Another strategy is the use of agents that block the receptors required to stimulate angiogenesis, such as antagonists to the vitronectin receptor. Yet a third strategy is the inhibition of specific enzymes which allow new blood vessels to invade surrounding tissues, for example, inhibitors of matrix metalloproteinases.

Angiogenesis is an attractive therapeutic target for cancer treatment due to its selectivity of action. Blood vessels in growing tumors are rapidly proliferating and being replaced, whereas blood vessels in most normal tissues are static. This rapid turnover is believed to be the physiological difference that will allow the selective targeting of blood vessels in the tumor by anti-angiogenic agents. Anti-angiogenesis is also less likely to pose a drug resistance problem compared to conventional chemotherapeutics. Tumor cells are prone to mutations that render them resistant to standard chemotherapy. Since anti-angiogenic agents target normal but rapidly proliferating endothelial cells that are not genetically unstable, resistance to anti-angiogenic agents is not a major concern.

Anti-angiogenic therapy will likely be very effective at suppressing tumor growth by denying tumors a blood supply. However, anti-angiogenic therapy may prove more effective in combination with other therapies aimed directly at the tumor cells. Chemical agents that demonstrate both anti-angiogenic and tumor directed properties would obviously be greatly desired. There thus remains a need to develop a series of chemical agents that demonstrate anti-proliferative effects against human endothelial cells for the treatment of a variety of diseases including cancer, in addition to an inhibitory effect directly on cancer cells for the treatment of solid tumors.

The present invention seeks to meet these and other needs.

The present description refers to a number of documents, the content of which is herein incorporated by reference in their entirety.

SUMMARY OF THE INVENTION

It has now been discovered that certain dibenzo[c]chromen-6-one derivatives have anti-proliferative abilities against both human endothelial cells and epithelial cancer cell lines and can be made as set forth herein.

The present invention relates to a series of chemical agents that demonstrate anti-proliferative effects against human endothelial cells for the treatment of a variety of diseases including cancer, in addition to an inhibitory effect directly on cancer cells for the treatment of solid tumors.

The present invention also relates to anti-cancer molecules that are derivatives of dibenzo[c]chromen-6-one.

As well, the present invention relates to a therapeutic composition of molecules useful in the treatment of cancer and other diseases, characterized by the undesired proliferation of endothelial or epithelial cells such as, but not limited to, pathological tissue growth, psoriasis, diabetic retinopathy, rheumatoid arthritis, hemangiomas, solid tumor formation and other malignancies.

In accordance with one embodiment of the present invention, there is provided a pharmaceutical composition, comprising a therapeutically effective amount of anti-cancer molecules specified herein. As used herein, the terms $R^1$, $R^2$, $R^3$ and $R^4$ refer to effective functional groups, whose location on the dibenzo[c]chromen-6-one backbone is illustrated below by Formula I:

Formula I

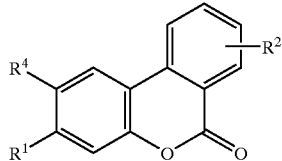

wherein $R^1$ is one of, but not limited to the following: H, OH or $OR^3$; wherein certain preferred substituents at $R^2$ are one of, but not limited to the following:

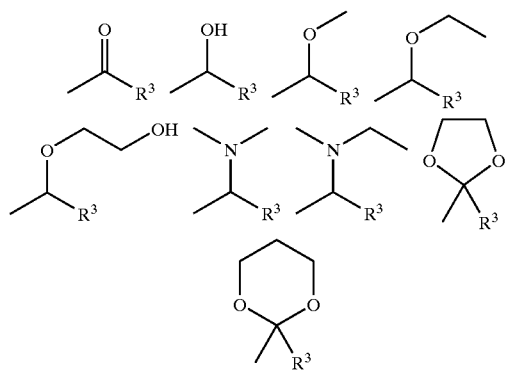

wherein certain preferred substituents at $R^3$ are one of, but not limited to the following: a lower alkyl chain ranging from 1 to 8 carbons; and wherein $R^4$ is selected from the group consisting of: hydrogen, hydroxy, methoxy, ethoxy and trifluoroethoxy.

In accordance with the present invention, there is therefore provided a compound of Formula I, or a pharmaceutically acceptable salt or ester thereof, Formula I

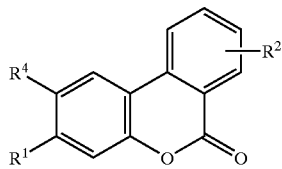

wherein $R^1$ represents a substituent selected from the group consisting of H, OH and $OR^3$; wherein $R^2$ represents a substituent selected from the group consisting of

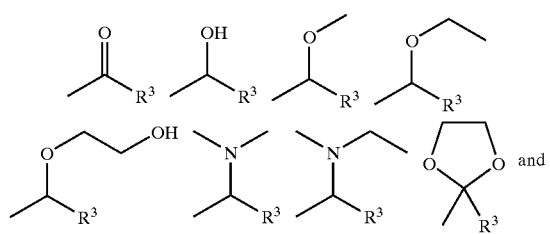

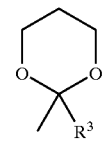

wherein $R^3$ is a $C_{1-8}$ lower alkyl chain and wherein $R^4$ is selected from the group consisting of: hydrogen, hydroxy, methoxy, ethoxy and trifluoroethoxy.

In accordance with the present invention, there is also provided a process for the preparation of a compound of Formula 1.5 involving the reaction of a molecule of Formula 1.4:

Formula 1.4

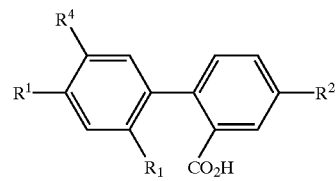

wherein $R^1$ represents a substituent selected from the group consisting of H, OH and $OR^3$; wherein $R^2$ represents a substituent selected from the group consisting of

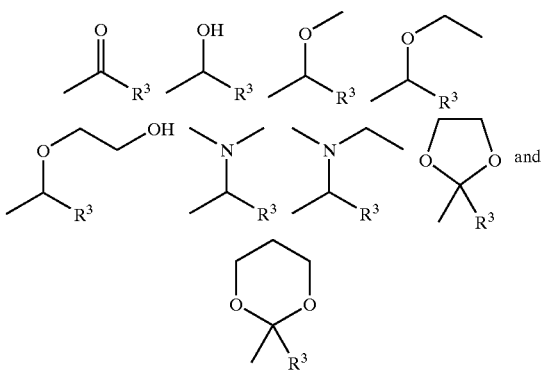

wherein $R^3$ is a $C_{1-8}$ lower alkyl chain; and wherein $R^4$ is selected from the group consisting of: hydrogen, hydroxy, methoxy, ethoxy and trifluoroethoxy; with a reagent mixture comprising $SOCl_2$ and $AlCl_3$, followed by the recovery of the compound of Formula 1.5 from the reaction mixture.

In accordance with the present invention, there is also provided a process for the preparation of a compound of Formula III, wherein $R^1$ is $OR^3$, wherein $R^2$ is

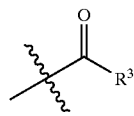

wherein $R^3$ is $CH_3$ and wherein $R^4$ is a methoxy group; involving the reaction of a compound of Formula 1.8:

Formula 1.8

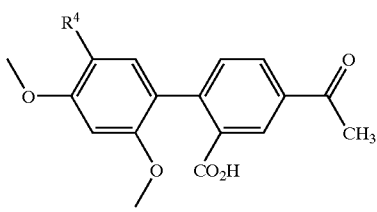

with a reagent mixture comprising $SOCl_2$ and $AlCl_3$, followed by the recovery of the compound of Formula III from the reaction mixture.

In accordance with the present invention, there is also provided a process for the preparation of a compound of Formula II, wherein $R^1$ is $OR^3$, wherein $R^2$ is

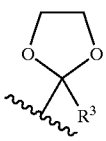

wherein $R^3$ is $CH_3$ and wherein $R^4$ is a methoxy group; involving the reaction of a compound of Formula 1.9:

Formula 1.9

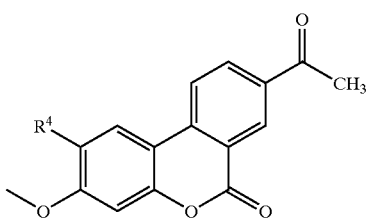

with a reagent mixture comprising $HOCH_2CH_2OH$ and p-TsOH, followed by the recovery of the compound of Formula II from the reaction mixture.

In accordance with the present invention, there is provided a pharmaceutical composition comprising the compound represented by Formula I and at least one pharmaceutically acceptable carrier.

In accordance with the present invention, there is also provided a process for the preparation of anti-cancer agents of Formula I, involving the reaction of a molecule of Formula 1.4, as previously defined, with a reagent system comprising $SOCl_2$ and $AlCl_3$, followed by the recovery of the anti-cancer agent of Formula I from the reaction mixture.

In accordance with the present inventions there is also provided a process for the preparation of an anti-cancer agent of Formula III, wherein $R^1$ is $OR^3$, wherein $R^2$ is

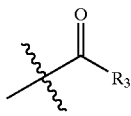

wherein $R^3$ is $CH_3$; and $R^4$ is a methoxy group; involving the reaction of a compound of Formula 1.8, as previously defined, with a reagent system comprising $SOCl_2$ and $AlCl_3$, followed by the recovery of the anti-cancer agent of Formula III from the reaction mixture.

Finally, in accordance with the present invention there is provided a process for the preparation of an anti-cancer agent of Formula II, wherein $R^1$ is $OR^3$, wherein $R^2$ is

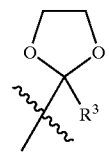

wherein $R^3$ is $CH_3$, and wherein $R^4$ is a methoxy group; involving the reaction of a compound of Formula 1.9, as previously defined, with a reagent mixture comprising $HOCH_2CH_2OH$ and p-TsOH, followed by the recovery of the anti-cancer agent of Formula II from the reaction mixture.

Unless defined otherwise, the scientific and technological terms and nomenclature used herein have the same meaning as commonly understood by a person of ordinary skill in the art. Generally, procedures such as recovering a—or more compounds from a reaction mixture are common methods used in the art. Such standard techniques can be found in reference manuals such as for example Gordon and Ford (The Chemist's Companion: A Handbook of Practical Data, Techniques and References, John Wiley & Sons, New York, N.Y., 1972).

The present description refers to a number of routinely used chemical terms. Nevertheless, definitions of selected examples of such terms are provided for clarity and consistency.

As used herein, the terminology "pharmaceutical composition" or "pharmaceutical formulation", well known in the art, are used interchangeably.

As used herein, the terminology "recovering", well known in the art, refers to a molecule having been isolated from other components of a reaction mixture.

The present invention comprises the genus of compounds represented by Formula I, useful in the treatment of cancer and other diseases characterized by the undesired proliferation of endothelial or epithelial cells such as, but not limited to, pathological tissue growth, psoriasis, diabetic retinopathy, rheumatoid arthritis, hemangiomas, solid tumor formation and other malignancies.

It will be appreciated by those skilled in the art that reference herein to treatment extends to prophylactic treatment as well as the treatment of established diseases or symptoms. It will be further appreciated, that the amount of a compound of the invention required for use in treatment, will vary with the nature of the condition being treated, the age and condition of the patient and will ultimately be at the discretion of the attending physician or medical practitioner. In general however, doses employed for adult human treatment will typically be in the range of 0.001 mg/kg to about 100 mg/kg per day. The desired dose may conveniently be presented in a single dose or as divided doses administered at appropriate intervals such as for example two, three, four or more sub-doses per day. It will be further appreciated by those skilled in the art that compounds of Formula I may be administered alone or in conjunction with standard tumor therapy, such as chemotherapy or radiation therapy.

The present invention also provides for novel pharmaceutical compositions of the compounds of Formula I. While it is possible that compounds of the present invention may be therapeutically administered as the raw chemical, it is preferable to present the active ingredient as a pharmaceutical formulation. Accordingly, the present invention further provides for pharmaceutical formulations comprising a compound of Formula I or a pharmaceutically acceptable salt or ester thereof together with one or more pharmaceutically acceptable carriers and, optionally, other therapeutic and/or prophylactic ingredients. The carrier(s) must be "acceptable" in the sense of being compatible with the other ingredients of the formulation and not be deleterious to the recipient thereof.

Formulations of the present invention, for the treatment of the indicated diseases, may be administered in standard manner, such as orally, parenterally, subligually, transdermally, rectally or via inhalation. For oral administration, the composition may take the form of tablets or lozenges, formulated in a conventional manner. For example, tablets and capsules for oral administration may contain conventional excipients such as binding agents, (for example, syrup, accacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) and wetting agents such as sodium lauryl sulphate. The tablets may be coated according to methods well known in the art.

Alternatively, the compounds of the present invention may be incorporated into oral liquid preparations such as aqueous or oily suspensions, solutions, emulsions, syrups or elixirs. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid.

Such preparations may also be formulated as suppositories, e.g., containing conventional suppository bases such as cocoa butter or other glycerides. Compositions for inhalation can be typically provided in the form of a solution, suspension or emulsion that may be administered as a dry powder or in the form of an aerosol using a conventional propellant such as dichlorodifluoromethane or trichlorofluoromethane. Typical transdermal formulations comprise a conventional aqueous or non-aqueous vehicle, such as creams, ointments, lotions or pastes or are in the form of a medicated plaster, patch or membrane.

Additionally, compositions of the present invention may be formulated for parenteral administration by injection or continuous infusion. Formulations for injection may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle (e.g., sterile, pyrogen-free water) before use.

Compositions of the present invention may be formulated for nasal administration. Such formulations may comprise the selected compounds of the present invention and a non-toxic pharmaceutically acceptable nasal carrier. Suitable non-toxic pharmaceutically acceptable nasal carriers for use in the compositions of the present invention will be apparent to those skilled in the art of nasal pharmaceutical formulations. Obviously the choice of suitable carriers will depend on the exact nature of the particular nasal dosage form desired, as well as on the identity of the active ingredient(s). For example, whether the active ingredient(s) are to be formulated into a nasal solution (for use as drops or spray), a nasal suspension, a nasal ointment or a nasal gel. Preferred nasal dosage forms are solutions, suspensions and gels, which contain a major amount of water (preferably purified water) in addition to the active ingredient(s). Minor amounts of other ingredients such as pH adjusters (e.g., a base such as NaOH), emulsifiers or dispersing agents (e.g. polyoxyethylene 20 sorbitan mono-oleate), buffering agents, preservatives, wetting agents and gelling agents (e.g. methylcellulose) may also be present. Also, a sustained release composition (e.g. a sustained release gel) can be readily prepared.

The composition according to the present invention may also be formulated as a depot preparation. Such long acting formulations may be administered by implantation (for example, subcutaneously or intramuscularly) or by intramuscular injection. Accordingly, the compounds of the present invention may be formulated with suitable polymeric or hydrophobic materials (such as an emulsion in an acceptable oil), ion exchange resins or, as sparingly soluble derivatives or sparingly soluble salts.

BRIEF DESCRIPTION OF THE DRAWINGS

Having thus generally described the invention, reference will now be made to the accompanying drawings, showing by way of illustration a preferred embodiment thereof, and in which:

FIG. 1 shows the effects of the compounds depicted by Formula II on the proliferation of four epithelial cancer cell lines;

FIG. 2 shows the effects of the compounds depicted by Formula III on the proliferation of four epithelial cancer cell lines;

FIG. 3 shows the effects of the compounds depicted by Formula II and III on the proliferation of HUVEC cells; and FIG. 4 shows the effects of the compounds depicted by Formula II and III on the proliferation of BBCE cells.

Other objects, advantages and features of the present invention will become more apparent upon reading the following non-restrictive description of preferred embodiments, with reference to the accompanying drawings, which are exemplary and should not be interpreted as limiting the scope of the present invention.

DESCRIPTION OF THE PREFERRED EMBODIMENT

The present invention is further illustrated by a series of new chemical agents that demonstrate anti-proliferative effects against human endothelial cells in addition to demonstrating an inhibitory effect directly on cancer cells for the treatment of solid tumors.

In one preferred embodiment of the invention, $R^1$ is $OR^3$, $R^2$ is

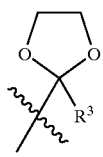

$R^3$ is $CH_3$ and $R^4$ is a methoxy group. Preferably at least one embodiment is represented by the following Formula II, or a pharmaceutically acceptable salt thereof:

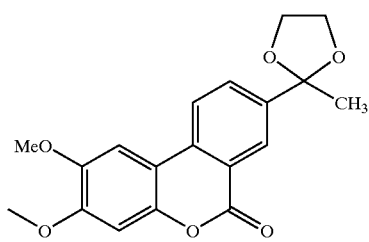

Formula II

In yet another preferred embodiment of the invention, $R^1$ is $OR^3$, $R^2$ is

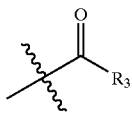

$R_3$ is $CH_3$ and R4 is a methoxy group. Preferably at least one embodiment is represented by the following Formula II, or a pharmaceutically acceptable salt thereof:

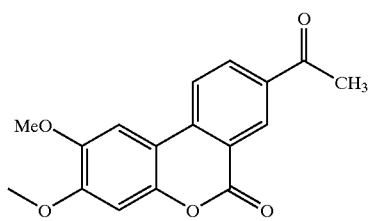

Formula III

Set forth below is a preferred synthesis scheme for the preparation of certain preferred embodiments of the anticancer molecules in accordance with the invention. The steps set forth below are set forth merely by way of examples. Those skilled in the art will readily recognize alternative synthetic pathways and variations capable of producing a variety of the dibenzo[c]chromen-6-one derivatives in accordance with the present invention.

A general process for the preparation of compounds of Formula I, is depicted in Schemes 1 and 2.

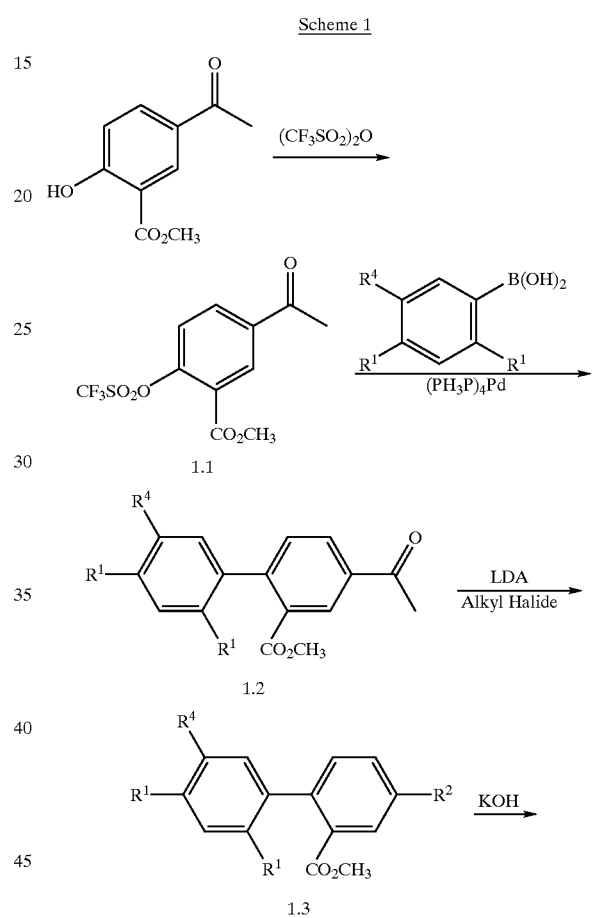

Scheme 1

Scheme 2
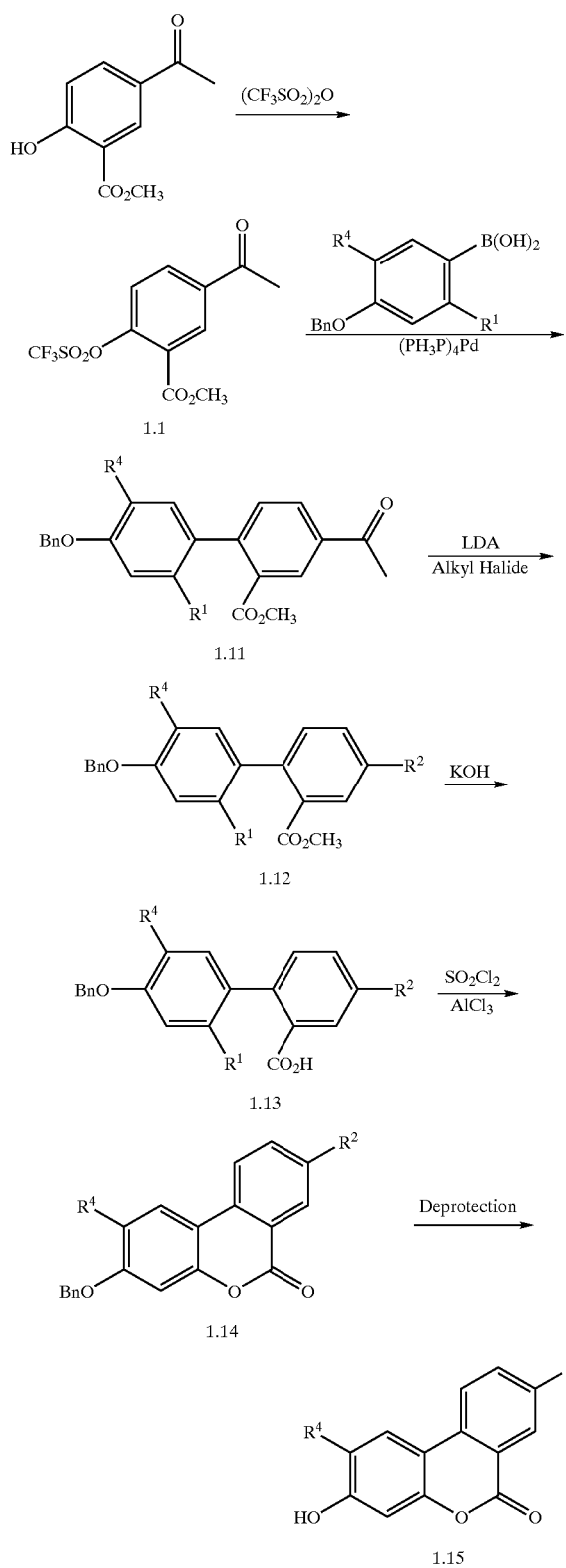
Scheme 3
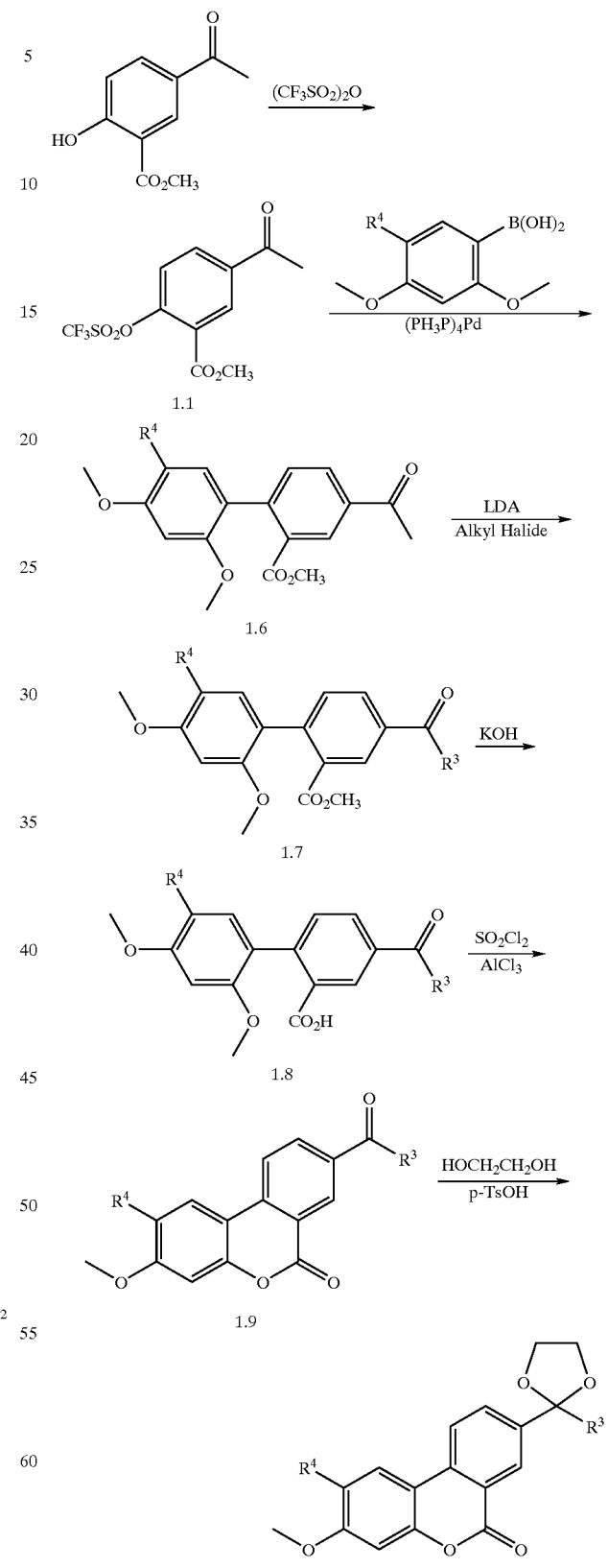
A process for the preparation of certain preferred embodiments for compounds of Formula I, is depicted in Scheme 3.

As depicted in Scheme 3, compound 1.1 is made by acylating methyl 5-acetyl salicylate using trifluoromethanesulfonic anhydride. Dimethoxyphenylboronic acid dissolved in a polar protic organic solvent, ethanol for example, was added to 1.1, dissolved in an organic solvent such as for example, 1,2-dimethoxyethane. An inorganic base such as potassium carbonate and a catalytic amount of tetrakis (triphenylphosphine)palladium was added and the mixture refluxed to give the biphenyl product 1.6. The formation of compound 1.7 can be accomplished via the alkylation of 1.6, using a strong base such as for example lithium diisopropylamide (LDA) and an alkyl halide. The saponification of 1.7 in an aqueous base such as potassium hydroxide at reflux affords the free acid biphenyl product 1.8. Cyclization to lactone 1.9, an example of one of the compounds represented by Formula I, occurs by treating 1.8 with thionyl chloride followed by treatment with aluminum trichloride, in a refluxing organic solvent such as 1,2-dichloroethane. Treatment of 1.9 with a diol such as ethylene glycol for example, in the presence of a catalytic amount of an acid such as p-toluenesulfonic acid, in a refluxing organic solvent affords 1.10, which is another example of one of the compounds represented by Formula I.

The present invention which is defined by the claims, is further illustrated by the following non-limiting examples.

EXAMPLE 1

Synthesis of 3-methoxy-8-(2-methyl-[1,3]-dioxolane-2-yl)-benzo[c]chromen-6-one

Step A: 5-acetyl-2-(trifluoromethylsulfonyloxy)-benzoic Acid, Methyl Ester

Methyl 5-acetylsalicylate (25 g, 129 mmol) was dissolved in $CH_2Cl_2$ (250 mL) and pyridine (60 mL) under argon at 0° C. Trifluoromethanesulfonic anhydride (37.9 g, 133 mmol) was then added over 20 min. The reaction was stirred for an additional 30 min and then quenched with water (500 mL). The organic layer was separated and washed three times with 5% HCl (80 mL). After removing the solvent, the solid obtained was dried under vacuum to yield 40.3 g (96%) of the title compound. $^1$H-NMR (400 MHz, $CDCl_3$) $\delta_H$ 2.56 (3H, s, $COCH_3$), 3.89 (3H, s, $OCH_3$), 7.32 (1H, d, ArH), 8.12 (1H, d, ArH), 8.52 (1H, s, ArH).

Step B: 4-acetyl-2',4'-dimethoxy-biphenyl-2-carboxylic Acid, Methyl Ester 2,4-Dimethoxyphenylboronic acid (24 g, 134 mmol) was dissolved in ethanol (250 mL). The compound from Step A (21 g, 67 mmol) was dissolved in 1,2-dimethoxyethane (375 mL). The two solutions were mixed with tetrakis (triphenylphosphine)palladium (1 g, 0.9 mmol) and $K_2CO_3$ (8.9 g, 64 mmol). The resulting suspension was refluxed for 2 h and then poured into saturated $NaHCO_3$ (1 L). The reaction mixture was extracted three times with $CH_2Cl_2$ (400 mL) and dried over $Na_2SO_4$. The solvent was removed to yield 35.6 g of crude product which was chromatographed on silica gel with hexane/ethyl acetate (2:1) followed by hexane/ethyl acetate (1:1) to yield 18.3 g (87%) of the title compound. $^1$H-NMR (400 MHz, $CDCl_3$) $\delta_H$ 2.68 (3H, s, $COCH_3$), 3.73 (3H, s, $OCH_3$), 3.76 (3H, s, $OCH_3$), 3.88 (3H, s, $CO_2CH_3$), 6.52 (1H, s ArH), 6.62 (1H, d, ArH), 7.23 (1H, d, ArH), 7.45 (1H, d, ArH), 8.13 (1H, d, ArH), 8.42 (1H, s, ArH).

Step C: Methyl 2'4'-dimethoxy-4-isobutyryl-2-biphenylcarboxylate

The compound from step B (1.03 g, 3.2 mmol) was dissolved in DME (40 ml) under argon and cooled to −20° C. and LDA (1.6 ml, 3.2 mmol) was added. The mixture was then warmed to room temperature and stirred for 30 min. Methyl iodide (0.2 ml, 3.2 mmol) was slowly added over 15 min. to give a cloudy suspension. The mixture was again cooled to −20 C. and a second portion of LDA (1.6 ml, 3.2 mmol) was added. After the mixture was warmed to room temperature and stirred for 30 min a second portion of methyl iodide (0.2 ml, 3.2 mmol) was added and the mixture stirred for 60 h. The mixture was added to cold $NaHCO_3$ (100 ml) and extracted with ethyl acetate (3×100 ml). The organic layer was washed with 5% HCl (3×25 ml) then dried and evaporated. The residue was chromatographed on silica gel with hexane/ethyl acetate (2:1) to give 0.208 g (24%) of the title compound. 1H-NMR (400 MHz, $CDCl_3$) $\delta_H$ 1.24 (6H, t, $CH(CH_3)_2$), 3.60 (1H, m, $CH(CH_3)_2$, 3.71 (3H, s, $OCH_3$), 3.89 (3H, s, $OCH_3$), 3.93 (3H, s, $OCH_3$), 6.86–8.32 (6H, ArH).

Step D: 4-acetyl-2',4'-dimethoxy-biphenyl-2-carboxylic Acid

The compound from Step C (9.3 g, 29.6 mmol) was mixed with distilled water (500 mL), and KOH (3.3 g, 59 mmol) added. The mixture was refluxed for 3 h and then acidified to pH 1 with concentrated HCl. The resulting precipitate was filtered and dried under vacuum at 45° C. for 3 h to yield 8.1 g (90%) of the title compound. $^1$H-NMR (400 MHz, $CDCl_3$) $\delta_H$ 2.71 (3H, s, $COCH_3$), 3.92 (3H, s, $OCH_3$), 3.96 (3H, s, $OCH_3$), 6.94 (1H, d, ArH), 6.96 (1H, s, ArH), 7.55 (1H, d, ArH), 8.17 (1H, d, ArH), 8.51 (1H, s, ArH).

Step E: 8-acetyl-3-methoxy-benzo[c]chromen-6-one

The compound from Step D was dissolved in 1,2-dichloroethane (60 mL) and $SOCl_2$ (1.7 mL, 23 mmol) was added. The mixture was refluxed for 90 min and then cooled to 0° C. at which point $AlCl_3$ (2.3 g, 17.3 mmol) was added. The resulting reaction mixture was stirred overnight at room temperature. The solvent was removed and the crude product chromatographed on silica gel with hexane/ethyl acetate (1:1) to yield 5.1 g (90%) of the title compound. $^1$H-NMR (400 MHz, $CDCl_3$) $\delta_H$ 2.74 (3H, s, $COCH_3$), 3.94 (3H, s, $OCH_3$), 6.92 (1H, s, ArH), 6.99 (1H, ArH), 8.02 (1H, d, ArH), 8.11 (1H, d, ArH), 8.41 (1H, d, ArH), 8.91 (1H, s, ArH).

Step F: 3-methoxy-8-(2-methyl-[1,3]-dioxolane-2-yl)-benzo[c]chromen-6-one

The compound from Step E (5.2 g, 19 mmol), ethylene glycol (4.4 g, 71 mmol) and a catalytic amount of p-toluenesulfonic acid (0.2 g) were dissolved in benzene (300 mL) and refluxed for 28 h. The solvent was removed and the crude product chromatographed on silica gel with hexane/ethyl acetate (2:1) to yield 3.6 g (60%) of the title compound. $^1$H-NMR (400 MHz, $CDCl_3$) $\delta_H$ 1.75 (3H, s, $CH_3$), 3.82 (2H, t, $OCH_2$), 3.91 (3H, s, $OCH_3$), 4.10 (2H, t, $OCH_2$), 6.93 (1H, s, ArH), 6.98 (1H, d, ArH), 7.47 (3H, m, ArH), 8.04 (1H, s, ArH).

EXAMPLE 2

Effectiveness of 3-methoxy-8-(2-methyl-[1,3]-dioxolane-2-yl)-benzo[c]chromen-6-One Against Endothelial Cells and Epithelial Cancer Cell Lines Those skilled in the art will appreciate that several acceptable cell proliferation assays are known and available for demonstrating the activity of the compounds of the present invention. The proliferation of endothelial cells is an important step in the process of blood vessel formation. Therefore, cells derived from the endothelium are useful in the study of angiogenesis and in vitro model systems utilising endothelial cells have the additional advantage of simplicity. Two model endothelial cell lines are the Human Umbilical Vein Endothelial Cells (HUVEC) and the Bovine Brain-derived Capillary Endothelial Cells (BBCE). Both have been used extensively to study the biology of endothelial cells. The following testing procedures were used.

Bovine Brain-Derived Capillary Endothelial Cells (BBCE)

BBCE are maintained in a regular medium containing DMEM plus 10% new-born calf serum and 2.5 mg/ml bFGF added every second day. Sub-confluent cells are collected, diluted to 5,000 cells per ml and seeded in 1 ml aliquots per well into 12-well cluster dishes. Cells are treated with drug candidates or the vehicle every second day. 2-methoxyestradiol is used as a positive control. After six days, the cells are washed and counted using a Coulter particle counter. The results are expressed as $IC_{50}$ values, that is, the concentration of the respective test compound resulting in half the number of cells that are obtained in controls.

Cancer Cells (MCF-7; MDA-MB-435; HCT-116; B16) & Human Umbilical Vein Endothelial Cells (HUVEC)

HUVEC are maintained in a M199 medium, supplemented with 90 mg/ml heparin, 2 mM L-glutamate, 10% foetal bovine serum (FBS), 90 mg/ml heparin sulphate, 20 mg/ml endothelial cell growth supplement, 100 mg/ml penicillin and 100 mg/ml streptomycin. The MCF-7, MDA-MB-435, HCT-116 and B16 cells are cultured in RPMI, D-MEM, RPMI and McCoy's 5R medium, supplemented with 10% glutamine, 1% non-essential amino acids (10 mM) and 1% sodium pyruvate (100 mM) respectively. All culture mediums are supplemented with 10% FBS. All cells are maintained in an atmosphere of 5% $CO_2$. Exponentially growing cells are seeded in 96-well plates and incubated for 16 hours. Cells are then treated continuously with the test articles and cell survival is evaluated 96 hours later by replacing the culture media with 150 μl fresh medium, containing 10 mM 4-(2-hydroxyethyl)-1-piperazineethanesulphonic acid buffer (pH 7.4). Next, 50 μl of 2.5 mg/ml of 3-(4,5-dimethylthiazo-2-yl)-2,5-diphenyltetrazolium bromide (MTT) in phosphate buffer solution (PBS) (pH 7.4), is added. After 3–4 hours of incubation at 37° C., the medium and MTT are removed and 200 μl of dimethylsulfoxide (DMSO) is added to dissolve the precipitate of reduced MTT, followed by the addition of 25 μl glycine buffer (0.1M glycine plus 0.1M NaCl, pH 10.5). The absorbance is determined at 570 nm with a microplate reader (BIORAD).

FIG. 1 shows the effects of the compound depicted by Formula II on the proliferation of four epithelial cancer cell lines. This is an indication that the compounds of the present invention are of potential in the treatment of a wide variety of cancers.

FIG. 3 shows the effects of the compound depicted by Formula II on the proliferation of HUVEC cells. This is an indication that the compounds of the present invention are of potential in the treatment of diseases characterized by the undesired proliferation of endothelial cells.

FIG. 4 shows the effects of the compound depicted by Formula II on the proliferation of BBCE cells. This is also an indication that the compounds of the present invention are of potential in the treatment of diseases characterized by the undesired proliferation of endothelial cells.

EXAMPLE 3

Effectiveness of 8-acetyl-3-methoxy-benzo[c]chromen-6-one Against Endothelial Cells and Epithelial Cancer Cell Lines The compound depicted by Formula III was tested using the same procedures as disclosed in Example 2 above.

FIG. 2 shows the effects of the compound depicted by Formula III on the proliferation of four epithelial cancer cell lines. This is an indication that the compounds of the present invention are of potential in the treatment of a wide variety of cancers.

FIG. 3 shows the effects of the compound depicted by Formula III on the proliferation of HUVEC cells. This is an indication that the compounds of the present invention are of potential in the treatment of diseases characterized by the undesired proliferation of endothelial cells.

FIG. 4 shows the effects of the compound depicted by Formula III on the proliferation of BBCE cells. This is also an indication that the compounds of the present invention are of potential in the treatment of diseases characterized by the undesired proliferation of endothelial cells.

The terms and descriptions used herein are preferred embodiments set forth by way of illustration only, and are not intended as limitations on the many variations which those skilled in the art will recognize to be possible in practicing the present invention. It is the intention that all possible variants whether presently known or unknown, that do not have a direct and material effect upon the way the invention works, are to be covered by the following claims.

Although the present invention has been described hereinabove by way of preferred embodiments thereof, it can be modified without departing from the spirit and nature of the subject invention as defined in the appended claims.

REFERENCES

App et al. U.S. Pat. No. 5,763,441 June 1995

Auerbach W and Auerbach R; Angiogenesis inhibition: a review. *Pharmacology and Therapeutics*, 1994; 63:265–311.

Backer et al. U.S. Pat. No. 5,843,925 December 1998

Beck L Jr and D'Amore P A; Vascular development: cellular and molecular regulation. *FASEB Journal*, Apr. 11, 1997 (5):365–73.

Blagosklonny M V, Schulte T, Nguyen P, Trepel J, Neckers L M; Taxol-induced apoptosis and phosphorylation of Bcl-2 protein involves c-Raf-1 and represents a novel c-Raf-1 signal transduction pathway. *Cancer Research* Apr. 15, 1996;56(8): 1851–4

Brooks et al. U.S. Pat. No. 5,753,230 March 1994

Colville-Nash P R and Willoughby D A; Growth factors in angiogenesis: current interest and therapeutic potential. *Molecular Medicine Today*, Jan. 14–23, 1997.

Coomber B L and Gotlieb A I; In vitro endothelial wound repair interaction of cell migration and proliferation. *Arteriosclerosis*. 1990; 10(2):215–222.

D'Amato et al. U.S. Pat. No. 5,504,074 April 1996

D'Amato et al. U.S. Pat. No. 5,593,990 January 1995

D'Amato et al. U.S. Pat. No. 5,629,327 May 1997

D'Amato et al. U.S. Pat. No. 5,712,291 June 1995

Eckhardt S G and Pluda J M; Development of angiogenesis inhibitors for cancer therapy. *Investigational New Drugs*, 1997; 15:1–3.

Fan T D, Jaggar R, and Bicknell R; Controlling the vasculature: angiogenesis, anti-angiogenesis and vascular targeting of gene therapy. *Trends in Pharmacological Sciences*, 1995; 16:57–66.

Fotsis et al. U.S. Pat. No. 5,643,900 March 1997

Gagliardi A and Collins D C; Inhibition of Angiogenesis by Anti-estrogens. *Cancer Research*, 1993; 53:533–535.

Galardy et al. U.S. Pat. No. 5,696,147 December 1993

Gastl G, Hermann T, Steurer M, Zmija J, Gunsilius E, Unger C, and Kraft A; Angiogenesis as a target for tumor treatment. *Oncology*, 1997; 54:177–184.

Harris A L, Zhang H, Moghaddam A, Fox S, Scott P, Pattison A, Gatter K, Stratford I, and Bicknell R. Breast cancer angiogenesis-new approaches to therapy via antiangiogenesis, hypoxic activated drugs, and vascular targeting. *Breast Cancer Research and Treatment,* 1996; 38:97–108.

Jain R K, Schlenger K, Hockel M, and Yuan F; Quantitative angiogenesis assays: Progress and problems. *Nature Medicine.* November 1997; 3(11):1203–1207.

Kumar R, Yoneda J, Bucana C D, and Fidler I J; Regulation of distinct steps of angiogenesis by different angiogenic molecules. *International Journal of Oncology.* 1998; 12(4):749–757.

Labudde J. A. and Heidelberger C; *J. Am. Chem. Soc.* 1958; 80:1225–1236.

Maier J A M, Delia D, Thorpe P E, Gasparini G; In vitro inhibition of endothelial cell growth by the antiangiogenic drug AGM-1470 (TNP-470) and the anti-endoglin antibody TEC-11. *Anti-Cancer Drugs,* 1997; 8:238–24.

Matsubara T, Saura R, Hirohata K, and Ziff M; Inhibition of human endothelial cell proliferation in vitro and neovascularization in vivo by D-penicillamine. *Journal of Clinical Investigation,* January 1989; 83:158–167.

Mousa S A; Mechanisms of angiogenesis in vascular disorders: potential therapeutic targets. *Drugs of the Future,* 1998; 23(1):51–60.

Nelson N J; Inhibitors of angiogenesis enter phase III testing. *Journal of the National Cancer Institute,* 1998; 90(13):960–963.

O'Reilly et al. U.S. Pat. No. 5,733,876 May 1995

O'Reilly M S; The preclinical evaluation of angiogenesis inhibitors. *Investigational New Drugs,* 1997; 15:5–13.

Petrow et al. U.S. Pat. No. 5,646,136 January 1994

Pluda J M; Tumor-associated angiogenesis: Mechanisms, clinical implications, and therapeutic strategies. *Seminars in Oncology,* April 1997; 24(2):203–218.

Risau W.; Mechanisms of angiogenesis. *Nature,* Apr. 17, 1997; 386(6626):671–4.

Singh Jai P. U.S. Pat. No. 5,610,166 March 1997

Szenkanecz Z, Szegedi G, and Koch A; Angiogenesis in rheumatoid arthritis: pathogenic and clinical significance. *Journal of Investigative Medicine,* 1998; 46:27–41.

Twardowski P and Gradishar W J; Clinical trials of antiangiogenic agents. *Current Opinion in Oncology,* 1997; 9:584–589.

Yamamoto T, Sudo K, and Fujita T; Significant inhibition of endothelial cell growth in tumor vasculature by an angiogenesis inhibitor, TNP-470 (AGM-1470). *Anticancer Research,* 1994; 14:1–4.

Zetter B R; Angiogenesis and tumor metastasis. *Annual Review of Medicine,* 1998; 49:407–424.

What is claimed is:

1. A compound of Formula I, or a pharmaceutically acceptable salt or ester thereof,

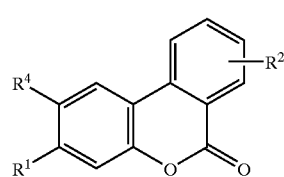

Formula 1 wherein:
i) $R^1$ represents a substituent selected from the group consisting of: H, OH and $OR^3$;
ii) $R^2$ represents a substituent selected from the group consisting of:

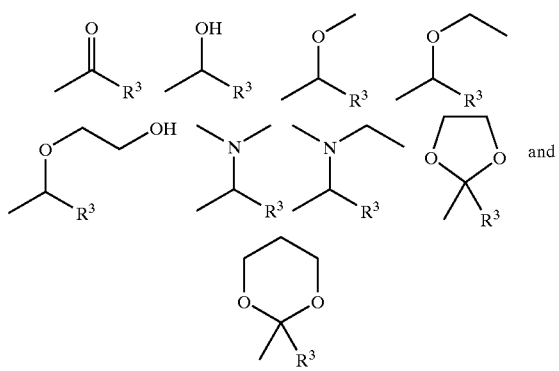

iii) $R^3$ is a $C_{1-8}$ lower alkyl chain; and
iv) $R^4$ is selected from the group consisting of: hydrogen, hydroxy, methoxy, ethoxy and trifluoroethoxy.

2. The compound of claim 1, wherein:
i) $R^1$ is $OR^3$;
ii) $R^2$ is

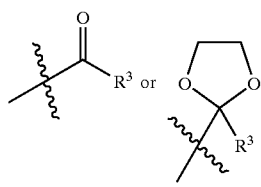

iii) $R^3$ is $CH_3$,
iv) $R^4$ is OMe.

3. The compound of claim 2, having the following formula:

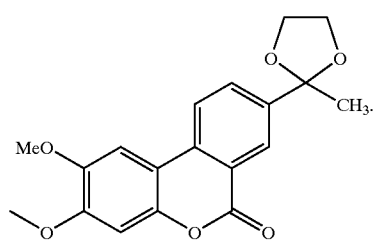

Formula II

4. The compound of claim 2, having the following formula:

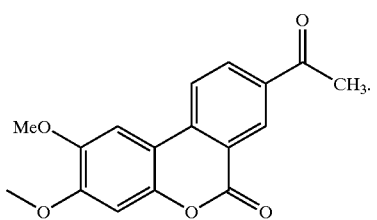

Formula III

5. A process for the preparation of a compound of Formula 1.5

Formula 1.5

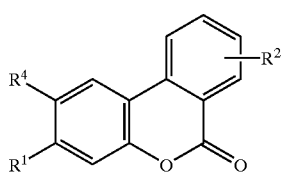

comprising:

a) reacting a molecule of Formula 1.4

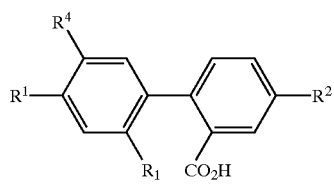

Formula 1.4 wherein i) $R^1$ represents a substituent selected from the group consisting of: H, OH and $OR^3$;

ii) $R^2$ represents a substituent selected from the group consisting of:

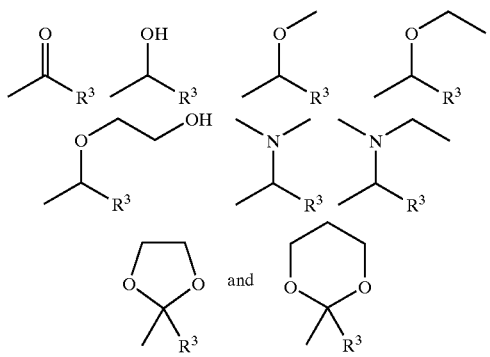

iii) $R^3$ is a $C_{1-8}$ lower alkyl chain; and iv) $R^4$ is selected from the group consisting of: hydrogen, hydroxy, methoxy, ethoxy and trifluoroethoxy with a reagent mixture comprising $SOCl_2$ and $AlCl_3$, thereby generating a reaction mixture, and b) recovering said compound of Formula 1.5 from said reaction mixture.

6. A process for the preparation of a compound of Formula III,

Formula III

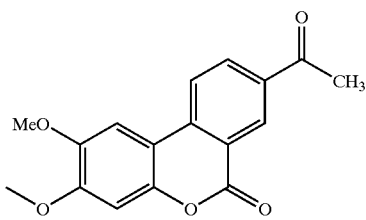

comprising:

a) reacting a molecule of Formula 1.8:

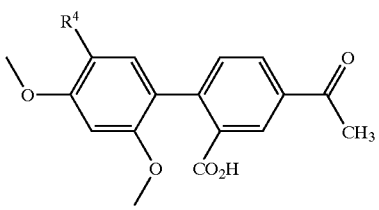

Formula 1.8 wherein $R^4$ is a methoxy group with a reagent mixture comprising $SOCl_2$ and $AlCl_3$, thereby generating a reaction mixture, and b) recovering said compound of Formula III from said reaction mixture.

7. A process for the preparation of a compound of Formula II,

Formula II

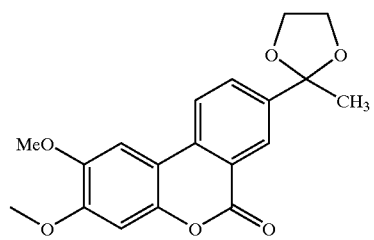

comprising:

a) reacting a molecule of Formula 1.9:

Formula 1.9

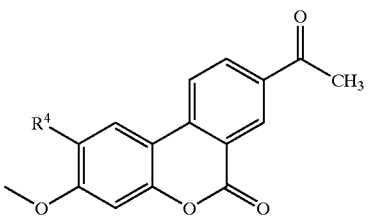

wherein $R^4$ it is a methoxy group with a reagent mixture comprising $HOCH_2CH_2OH$ and p-TsOH, thereby generating a reaction mixture, and b) recovering said compound of Formula II from said reaction mixture.

8. A pharmaceutical composition comprising the compound of Formula I or a pharmaceutically acceptable salt or ester thereof and at least one pharmaceutically acceptable carrier.

9. A method of treating cancer comprising administering a therapeutically effective amount of the compound of Formula I to a patient in need thereof.

10. The compound of claim 1, wherein said compound is a compound of Formula 1.5 or a pharmaceutically acceptable salt or ester thereof, Formula 1.5

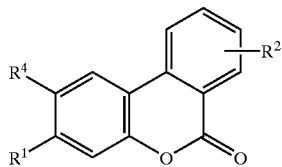

wherein:
 i) $R^1$ represents a substituent selected from the group consisting of: H, OH and $OR^3$;
 ii) $R^2$ represents a substituent selected from the group consisting of

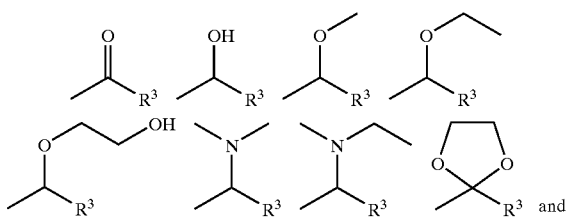

iii) $R^3$ is a $C_{1-8}$ lower alkyl chain; and
 iv) $R^4$ is selected from the group consisting of: hydrogen, hydroxy, methoxy, ethoxy and trifluoroethoxy.

11. The pharmaceutical composition of claim 8, wherein said compound is a compound of Formula II.

12. The pharmaceutical composition of claim 8, wherein said compound is a compound of Formula III.

13. The method of treating cancer of claim 9, wherein said compound is a compound of Formula II.

14. The method of treating cancer of claim 9, wherein said compound is a compound of Formula III.

* * * * *

UNITED STATES PATENT AND TRADEMARK OFFICE
CERTIFICATE OF CORRECTION

PATENT NO. : 6,632,835 B2
APPLICATION NO. : 09/934086
DATED : October 14, 2003
INVENTOR(S) : Jonathan Martin Schmidt It is certified that error appears in the above-identified patent and that said Letters Patent is hereby corrected as shown below:

In column 19, lines 1-8 (claim 5), Formula 1.5 should be represented as:

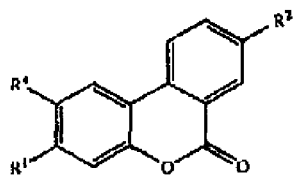

In column 21, lines 1-8 (claim 10), Formula 1.5 should be represented as:

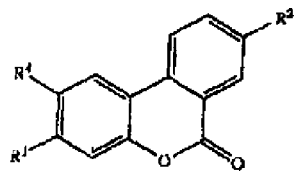

Signed and Sealed this

Twenty-eighth Day of April, 2009

JOHN DOLL
*Acting Director of the United States Patent and Trademark Office*